United States Patent [19]

Snyder et al.

[11] Patent Number: 5,334,503
[45] Date of Patent: Aug. 2, 1994

[54] TEST KIT AND METHOD FOR THE DETECTION OF MICROORGANISMS ASSOCIATED WITH PERIODONTAL DISEASES USING SURFACTANT MIXTURE AS EXTRACTION COMPOSITION

[75] Inventors: Brian A. Snyder; Paul B. Contestable; Catherine T. Abrams; Elizabeth A. Grogan, all of Rochester, N.Y.

[73] Assignee: Eastman Kodak Company, Rochester, N.Y.

[21] Appl. No.: 773,833

[22] Filed: Oct. 8, 1991

[51] Int. Cl.$^5$ ............................................. G01N 33/569
[52] U.S. Cl. ..................................... 435/7.32; 435/7.9; 435/7.92; 435/7.94; 435/961; 435/975; 435/259
[58] Field of Search ................ 435/5, 7.32, 7.33, 7.34, 435/7.35, 7.36, 7.37, 961, 259; 436/174, 175; 252/351, 352, 357, 173

[56] References Cited

U.S. PATENT DOCUMENTS

| | | | |
|---|---|---|---|
| 3,560,390 | 2/1971 | Gaines | 252/107 |
| 4,282,001 | 8/1981 | Klose et al. | 23/230 |
| 4,430,437 | 2/1984 | Hampar et al. | 436/548 |
| 4,497,899 | 2/1985 | Armstrong et al. | 436/510 |
| 4,497,900 | 2/1985 | Abram et al. | 436/511 |
| 4,661,349 | 4/1987 | Kino et al. | 424/89 |
| 4,695,537 | 9/1987 | Dorsett | 435/5 |
| 4,741,999 | 5/1988 | Genco et al. | 435/7.32 |
| 4,866,167 | 9/1989 | Chen et al. | 536/27 |
| 4,959,303 | 9/1990 | Milburn et al. | 435/7.36 |
| 5,081,010 | 6/1992 | Cummins et al. | 435/5 |
| 5,132,205 | 7/1992 | Pronovost et al. | 435/5 |

FOREIGN PATENT DOCUMENTS

| | | | |
|---|---|---|---|
| 085448 | of 0000 | European Pat. Off. | |
| 338591 | of 0000 | European Pat. Off. | |
| 1365 | 4/1979 | European Pat. Off. | |
| 183215 | 6/1986 | European Pat. Off. | |
| 269388 | 6/1988 | European Pat. Off. | 435/7.32 |
| 363110 | 4/1990 | European Pat. Off. | |
| 382519 | 8/1990 | European Pat. Off. | |
| 187862 | 11/1983 | Japan | 435/7.94 |
| 87/02678 | 5/1987 | World Int. Prop. O. | |

OTHER PUBLICATIONS

Microparticle Immunoassay Techniques, 2nd Ed., Seradyn, Inc., pp. 4–7 and 41–49 (1988).

*Primary Examiner*—Carol E. Bidwell
*Attorney, Agent, or Firm*—J. Lanny Tucker

[57] ABSTRACT

An extraction composition is described which is buffered to a pH from about 8 to about 11 and which contains from about 1 to about 10 weight percent of a water-soluble cationic surfactant which is a quaternary ammonium salt or a mixture thereof and from about 1 to about 10 weight percent of an anionic surfactant which has a sulfate anion having from 6 to 14 carbon atoms and an alkali metal or ammonium cation. The extraction composition is used to extract antigens from *Actinobacillus actinomycetemcomitans*, *Porphyromonas gingivalis* or *Prevotella intermedia*. Extracted antigens are determined using immunological methods. The extraction composition can be supplied as part of a diagnostic test kit.

12 Claims, No Drawings

TEST KIT AND METHOD FOR THE DETECTION OF MICROORGANISMS ASSOCIATED WITH PERIODONTAL DISEASES USING SURFACTANT MIXTURE AS EXTRACTION COMPOSITION

FIELD OF THE INVENTION

The present invention relates to a diagnostic test kit and a method for using a surfactant mixture to extract and determine microorganisms associated with periodontal diseases. In particular, the method is useful for the extraction and determination of an antigen from any of the microorganisms *Actinobacillus actinomycetemcomitans*, *Prevotella intermedia* (formerly known as *Bacteroides intermedius*) or *Porphyromonas gingivalis* (formerly known as *Bacteroides gingivalis*).

BACKGROUND OF THE INVENTION

There is a continuous need in medical practice, research and diagnostic procedures for rapid, accurate and qualitative or quantitative determinations of biological substances which are present in biological fluids at low concentrations. For example, the presence of drugs, narcotics, hormones, steroids, polypeptides, prostaglandins or infectious organisms in blood, urine, saliva, vaginal secretions, dental plaque, gingival crevicular fluid and other biological specimens has to be determined in an accurate and rapid fashion for suitable diagnosis or treatment.

To provide such determinations, various methods have been devised for isolating and identifying biological substances employing specific binding reactions between the substance to be detected (sometimes identified as a "ligand") and a compound specifically reactive with that substance (sometimes identified as a "receptor").

Extraction of antigen from microorganisms of interest in a biological specimen is generally critical to providing an accurate, rapid and sensitive assay. Many varied techniques have been used for extraction including physical disruption of the cells by sonication, heating or centrifugation. Chemical extraction compositions have also been developed. For example, various surfactants, such as sodium dodecyl sulfate, have been used individually in extraction compositions.

Specific microorganisms have been implicated as indicators for a number of periodontal diseases in humans and animals, such as gingivitis and periodontitis. The importance of such diseases is growing in the human population, especially as people live longer, and prevention of such diseases is becoming of considerable importance to dentists, insurance carriers and the health industry in general. In addition, proper dental care for animals is a growing concern in our culture.

Detection of microorganisms associated with periodontal diseases has been accomplished using culture techniques, DNA probes and a number of immunological procedures, such as agglutination assays, enzyme linked immunosorbent assays (ELISA) and others known in the art. ELISA utilizes the reaction of an extracted antigen from the microorganism(s) and the corresponding antibody to form an immunological complex. As noted above, usually uncomplexed materials are washed from the complex in order to provide an accurate assay result.

An advance in the art in the detection of microorganisms associated with periodontal diseases is described and claimed in U.S. Ser. No. 468,392 (filed Jan. 22, 1990 by Snyder). This case describes the simultaneous detection and differentiation of these microorganisms, and particularly *Actinobacillus actinomycetemcomitans*, *Porphyromonas gingivalis* and *Prevotella intermedia*, in an immunometric (also known as "sandwich") assay using water-insoluble reagents in defined regions of a microporous filtration membrane. Antigens from the microorganisms were extracted using a 10% (by weight) solution of sodium dodecyl sulfate.

While the noted simultaneous assay represents an important advance in the art for detecting the noted microorganisms, in some cases, unacceptable background was observed, especially when clinical specimens were tested. It was also noticed that the known surfactant extraction composition did not adequately extract antigen from all serotypes of the microorganisms of interest. A solution to this problem is critical since it is highly important for the user of the assay to discriminate among the microorganisms for effective diagnosis and treatment of disease without significant background. It would also be useful to have a universal extraction composition that could be used to extract all serotypes of related microorganisms.

SUMMARY OF THE INVENTION

The problems noted above have been overcome using a diagnostic test kit comprising in separate packaging:

(1) an aqueous composition buffered to a pH of at least about 8 comprising:
  a. at least about 0.05 weight percent of a water-soluble cationic surfactant, and
  b. at least about 0.05 weight percent of an anionic surfactant, and (2) at least one kit component selected from the group consisting of:
  (a) a detectably labeled, water-soluble receptor for a specific binding ligand of interest,
  (b) a disposable test device,
  (c) a wash composition for separating uncomplexed materials from a complex of a ligand of interest and its receptor, the composition comprising at least one surfactant,
  (d) a composition for providing a colorimetric, fluorometric or chemiluminescent signal in the presence of an enzyme label, and
  (e) a receptor for a ligand of interest, which receptor is insolubilized, or capable of being insolubilized.

A method for the extraction of an antigen from a microorganism or virus comprises:
  contacting a specimen suspected of containing a microorganism or virus of interest with an aqueous composition buffered to a pH of at least about 8 comprising:
    a. at least about 0.05 weight percent of a water-soluble cationic surfactant, and
    b. at least about 0.05 weight percent of an anionic surfactant,
    the contacting being carried out under time and temperature conditions effective to extract an antigen from the microorganism or virus.

Further, a method for the determination of a microorganism or virus comprises:

A. contacting a specimen suspected of containing a microorganism or virus of interest with an aqueous extraction composition buffered to a pH of at least about 8 comprising:
a. at least about 0 05 weight percent of a water-soluble cationic surfactant, and
b. at least about 0.05 weight percent of an anionic surfactant, and
the contacting being carried out under time and temperature conditions effective to extract an antigen from the microorganism or virus,
B. forming a detectable immunological complex of the extracted antigen and an antibody specific to the antigen, and
C. detecting the complex as a determination of the presence of the microorganism or virus in the specimen.

The present invention provides a means for rapid and sensitive detection of microorganisms associated with periodontal diseases. In particular, this invention allows for rapid extraction and detection of all serotypes of those microorganisms using a universal extraction composition. Thus, while known extraction compositions effectively extract some microorganisms or serotypes thereof, the composition described herein extracts all serotypes of related microorganisms.

These advantages are achieved using a universal extraction composition which includes both a water-soluble cationic surfactant and an anionic surfactant. The composition is also critically buffered to a relatively high pH, that is at least about 8. This composition provides better extraction than other extraction compositions, and the background in the assays is considerably reduced while maintaining suitable assay sensitivity for targeted antigens.

DETAILS OF THE INVENTION

The present invention provides a diagnostic test kit that can be used in any specific binding assay whereby a ligand of interest is extracted from a microorganism (or other organism or component thereof) or virus particle, complexed with its corresponding receptor, and the complex is detected in a suitable manner. Ligands which can be so detected are well known in the art and include, but are not limited to, antigenic proteins and carbohydrates, toxins, lectins, enzymes, polysaccharides, glycolipids, antibodies, nucleic acids, amino acids, peptides, polypeptides, glycoproteins and any components of the foregoing materials. Preferably, this invention is used in the extraction and detection of immunological materials which are defined herein as materials, which when injected into an immunocompetent host, will produce an immunological response (that is, cause the production of antibodies specific to those materials), as well as the antibodies so produced.

The method to detect a ligand of interest can be used to assay any human or animal biological fluid or specimen of interest including, but not limited to, whole blood, plasma, sera, lymphatic fluid, bile, urine, spinal fluid, seminal fluid, vaginal secretions, sputum, perspiration, stool specimens, fluid preparations of tissues, periodontal tissue, dental plaque, crevicular fluid and saliva.

It is to be understood that while the remaining discussion is directed to microorganisms associated with periodontal diseases, the utility of the kit of this invention is not so limited. Rather, the following discussion is provided merely for exemplification of their preferred uses.

The extraction composition described herein is an aqueous buffered solution which keeps background low, especially when several ligands are being detected simultaneously in the same test device. This is seen in the examples below relating to simultaneous detection of microorganisms associated with periodontal diseases.

The extraction composition is buffered to a relatively high pH, that is about 8 or above. Preferably, the pH of the composition is from about 8 to about 11 with a pH of about 8.5 being most preferred.

The appropriate pH can be provided by the use of an appropriate amount of one or more appropriate buffers. A base, such as a hydroxide, may be added to raise the pH to that needed for a given buffer. Organic or inorganic buffers which are well known in the art, include but are not limited to, glycine, phosphate, 2-(N-morpholino)ethanesulfonic acid, 3-(cyclohexylamino)-1-propanesulfonic acid, 3-(cyclohexylamino)-2-hydroxy-1-propanesulfonic acid, 2-(N-cyclohexylamino)ethanesulfonic acid, and any others which provide buffering at the desired pH and which do not adversely affect the antigen being extracted. The amount of each buffer would depend upon its buffering strength and what pH is desired. This could be readily determined by one of ordinary skill in the art, and generally is at least about 0.01 molar. Glycine is a preferred buffer.

One essential component of the extraction composition is a water-soluble cationic surfactant. A mixture of surfactants can be used if desired. By water-solubility is meant that up to about 0.5 mg of the compound is soluble in 1 ml water at room temperature. Water-solubility is important to provide optimum access to the antigens being extracted and maintain desired flow characteristics of the resulting solution of extracted antigen, which solution may include some cellular debris.

Generally the useful cationic surfactants have one or more cationic groups selected from the group consisting of quaternary ammonium salts, quaternary phosphonium salts, quaternary pyridinium salts, quaternary imidazolium salts and mixtures of any of these. Quaternary ammonium salts are preferred. Generally any cationic surfactant is useful in the present invention as long as it does not adversely affect the antigen being extracted. Many such cationic surfactants meeting those requirements are known in the art, and can be evaluated by routine experimentation by mixing a given concentration of surfactant with a given microorganism under extraction conditions (described below) to see if sufficient antigen is extracted for assay. Most known cationic surfactants are not easily characterized by chemical structures, but many of them are commercially available from manufacturers listed in the patent and trade literature. One standard source of such information is *McCutcheon's Emulsifiers and Detergents*, 1986 (or later editions), McCutcheon Division, Publishing Co., Glen Rock, N.J.

Useful cationic surfactants include, but are not limited to, nonpolymeric aliphatic, heterocyclic or carbocyclic compounds having a molecular weight less than about 3000. Preferably, these compounds are aliphatic, heterocyclic or carbocyclic quaternary ammonium compounds. See, for example, EP-A-0,085,448 (published Jun. 10, 1988).

As used herein, "aliphatic" refers to an organic cationic compound which contains aliphatic (or open-chain) groups connected to the heteroatom (for example, a phosphorus or nitrogen) which provides the positive charge. These groups contain from 1 to 30 carbon atoms and can have oxygen or sulfur atoms interspaced along the chain, provided each compound has at least 1 carbon atom. One or more hydrogen atoms along any aliphatic chain can be replaced with fluorine atoms to provide a fluorinated group. The groups can also be substituted with one or more other halo atoms, aryl, alkoxy, amino, cycloalkyl or other groups as would be apparent to one skilled in the art.

As used herein, the term "heterocyclic" refers to an organic cationic compound having at least one heterocyclic moiety attached to the atom providing the cationic charge. The cationic charge can be within the heterocyclic group if desired, or in another portion of the molecule. It can be aromatic or nonaromatic and can contain nitrogen, sulfur, oxygen or selenium atoms as well as carbon atoms. Generally, the heterocyclic moiety has from 5 to 15 atoms (other than hydrogen atoms) in the mono- or polycyclic ring or nucleus and can be substituted with one or more other organic groups if desired as would be apparent to one skilled in the art.

The term "carbocyclic" refers to an organic compound having one or more carbocyclic moieties attached to the atoms providing the cationic charge. Such moieties include cycloalkyl generally of 5 to 20 carbon atoms, cycloalkenyls generally of 5 to 20 carbon atoms, and aryls generally of 6 to 14 carbon atoms, in the mono- or polycyclic ring or nucleus. They can be unsubstituted or substituted with one or more other organic groups as would be apparent to one skilled in the art.

Representative cationic surfactants useful in this invention include polypropoxy quaternary ammonium chlorides, acetates and phosphates (marketed under the trademark EMCOL from Witco Chemical Co.), fatty acid amidoalkyldimethyl amines (marketed under the trademark SCHERCODINE from Scher Chemical Co.), ethoxylated fatty amines (marketed under the trademark PEGAMEENS from Borg-Warner Chemical Co.), long-chain alkyldiethanol methyl quaternary ammonium chlorides (marketed under the trademark M-QUAT from Mazer Chemical Co.), fatty acid derivatives of imidazolines (marketed under the trademark MONAZOLINE from Mona Industries) and longchain alkylhydroxyethyl imidazolines (marketed under the trademark ALKAZINE from Alkaril Chemical Co.). Most useful surfactants are the quaternary ammonium salts of polypropoxy-t-amine or a mixture thereof (such as those marketed as EMCOL TM CC-9, CC-36, CC-55 and CC-57 for example). EMCOL TM CC-9 is most preferred.

Other useful cationic surfactants include, but are not limited to, nonyltrimethyl ammonium bromide, dodecyltrimethyl ammonium chloride, hexadecyltrimethyl ammonium bromide, hexadecylpyridinum bromide, benzyltriethyl ammonium chloride, didodecyldimethyl ammonium bromide, benzyldimethylphenyl ammonium chloride, tetrahexyl ammonium chloride, stearyldimethylbenzyl ammonium chloride and polypropoxy quaternary ammonium chlorides.

The amount of cationic surfactant useful in the composition is at least about 0.05 percent (based on total composition weight). The upper limit is not critical and can be as high as solubility of the compound and practical considerations allow. Preferably, the amount is from about 1 to about 10 weight percent. The amount may be adjusted for various surfactants to obtain the optimum results. A particularly useful extraction composition is shown in Example 1 below which also shows optimum amounts for specific surfactants and buffer.

A second essential component of the extraction composition is an anionic surfactant. In the broadest sense of this invention, the anionic surfactant can be any water-soluble or water-dispersible compound which has a net negative charge and which has the general properties attributed to anionic surfactants. The McCutcheon's publication cited above is a good source for finding useful compounds. Again, a given surfactant can be tried in the extraction composition to see if suitable extraction occurs as a means for determining if it is useful in the practice of this invention.

As useful classes of anionic surfactants, one can consider carboxylate and sulfonate salts (such as alkylbenzenecarboxylates, alkylbenzenesulfonates, alkylsulfonates, sulfosuccinate ester salts, formalin condensates of naphthalene and alkylnaphthalenesulfonates), sulfate ester salts (such as alkylsulfate ester salts, polyoxyalkylene alkyl ether sulfate ester salts or polyoxyalkylene alkylaryl ether sulfate ester salts) and phosphate ester salts (such as alkyl phosphate ester salts, polyoxyalkylene alkyl ether phosphate ester salts or polyoxyalkylene alkylaryl ether phosphate ester salts). Others, including cholic acid and salts thereof (such as deoxycholate), would be readily apparent to one skilled in the art.

In a preferred embodiment, the anionic surfactant comprises an alkyl sulfate anion having from 6 to 14 carbon atoms (either linear or branched chain, for example hexyl, octyl, decyl, 2-methylhexyl, dodecyl and tetradecyl), and an alkali metal or ammonium cation.

Preferably, the sulfate anion has from 8 to 12 carbon atoms with decyl sulfate and dodecyl sulfate being most preferred. Representative alkali metal cations include, but are not limited to, lithium, sodium, potassium and rubidium. Useful surfactants include, but are not limited to, ammonium decyl sulfate, sodium dodecyl sulfate, potassium decyl sulfate, lithium hexyl sulfate and sodium tetradecyl sulfate. The corresponding acids of these compounds may also be useful. Sodium dodecyl sulfate is the most preferred compound. A mixture of anionic surfactants can be used if desired.

The anionic surfactant is generally present in the extraction composition in an amount of at least about 0.05 percent (based on composition weight). The upper limit of concentration is not critical and can be as high as the compounds solubility and practical considerations allow. Preferably, the amount is from about 1 to about 10 weight percent.

While not preferred, optional components of the extraction composition include protein carriers such as bovine serum albumin, casein or similar materials, reducing agents such as dithiothrietol, and alcoholamines (such as ethanolamine).

The extraction composition can be prepared merely by mixing the cationic and anionic surfactants in a suitable buffer. It can be used immediately for extracting a ligand, or stored in a suitable container for later use, for example as part of a diagnostic test kit.

Such kits can include, in individual packaging or containers, the extraction composition and one or more of a number of other kit components, such as reagents, compositions and assay apparatus or devices needed for a given assay. These kit components are listed above in the Summary of the Invention, and described in more detail below. Preferably, the kit includes all of the components listed above, and optionally others not listed but which would commonly be included in a diagnostic test kit. In a most preferred embodiment, the kit includes, as a ligand receptor, an antibody specific for an antigen extracted from a microorganism associated with periodontal disease, such as an antibody for any of *Actinobacillus actinomycetemcomitans*, *Prevotella intermedia* and *Porphyromonas gingivalis*.

It is also preferred that the receptor for a specific binding ligand of interest be detectably labeled (for example with an enzyme or other labeling means) or immobilized on a suitable substrate. Other components of a kit can include detection means such as dye providing compositions (described in more detail below), assay devices, wash compositions, insolubilizing reagents (described below), instructions, pipettes and other apparatus needed for a typical assay. In a more preferred embodiment, the kit includes a disposable test device (described below), and an antibody for the extracted antigen which is immobilized on a particulate substrate, membrane (including polymeric and cellulosic filters), cellulosic sheet or polymeric film. Such a kit can be assembled and sold with all components present, or provided as individual parts prior to use in an assay.

Extraction is generally accomplished by contacting (such as by mixing) a specimen suspected of containing the microorganism, virus or other analyte of interest with the extraction composition described herein under time and temperature conditions effective to extract sufficient antigen for detection.

The time and temperature will, of course, vary depending upon the strength of the surfactants, the sensitivity of assay desired, the amount of analyte present and other factors that one skilled in the art would be aware of. The time and temperature may also vary inversely, for example, with more time needed for extraction at lower temperatures.

In general, extraction will be carried out at temperatures above about 15° C. up to the boiling point of water (at atmospheric pressure), with temperatures in the range of from about 15° to about 40° C. being preferred and room temperature (18°-25° C.) being most preferred. The time for extraction can vary greatly from a few seconds up to several minutes, but it is generally from about 10 seconds to about 60 minutes, with from about 30 seconds to about 10 minutes being most preferred. Moreover, the specimen and extraction composition can be mixed and stored for months prior to assay for the antigen, so there is considerable latitude in the time used for extraction. For practical purposes, however, it usually requires less than a hour.

Extraction can be carried out in a suitable container (such as test tubes, beakers and cuvettes), although some devices have been fashioned specifically for extraction purposes (see for example, U.S. Pat. No. 4,746,614 issued May 24, 1988 to Devaney, Jr. et al). Once a ligand (such as an antigen) is extracted from host cells, virus particle or organism, it may be desirable to remove cellular debris, particulate matter or other unwanted materials by filtration or another means. Prefiltering can be carried out using suitable devices fashioned for that purpose which may also be designed for extraction methods (for example as described in U.S. Pat. No. 4,746,614), or by merely using filter paper.

The extracted antigen can be detected in a number of analytical procedures to detect its presence or amount. Such procedures include, radial immunodiffusion, immunoelectrophoresis and serological tests which, while not preferred, but be the only choice in certain instances. Details of useful procedures are known in the art [e.g., see Rose et al (Eds.), *Manual of Clinical Laboratory Immunology*, 3rd Edition, American Society for Microbiology, Washington, D.C., 1986, Chapter 74 (Fucillo et al)].

Preferably, the extracted antigen is detected using an immunoassay in which it is immunologically reacted with one or more antibodies specific thereto. The resulting immunological complex is detected using suitable techniques including turbidimetric, reflectance, radiometric, colorimetric, fluorometric or chemiluminescent procedures.

In particular, the microorganisms *Actinobacillus actinomycetemcomitans*, *Porphyromonas gingivalis* and *Prevotella intermedia* are determined, either individually or collectively, using the present invention by extracting antigens from one or all of the serotypes of the microorganisms and detecting each accordingly. However, other microorganisms which are suspected of being associated with periodontal diseases can also be detected or differentiated with this invention. Such other microorganisms include, but are not limited to, *Wolinella recta*, *Bacteroides forsythus*, *Eikenella corrodens*, *Fusobacterium nucleatum* and *Treponema denticola*. In some embodiments, it is irrelevant as to which serotypes of any of the microorganisms may be present. In other embodiments, the invention can be used to differentiate among serotypes of a single species as well as among species.

The method of this invention is generally qualitative although the amount of immunological complex can be observed and correlated to the amount of antigen in a specimen. Thus, the assay can be quantitative also.

Antibodies useful in the practice of this invention can be monoclonal or polyclonal. Monoclonal antibodies can be prepared using standard procedures, such as those described in U.S. Pat. No. 4,741,999 (noted above). Polyclonal antibodies can also be produced using standard procedures, such as described by Zambon et al, *Infect. & Immun.*, 41(1), pp. 31-36, 1985. Generally, a mammal is immunized one or more times with a suitable quantity of an antigenic component or whole bacterial cells of the organism. After a suitable time, when the titer is acceptable, antisera is recovered from the mammal. Antibodies can be removed from antisera and purified if desired using known procedures and stored in frozen buffered solutions until used. A preferred method for providing highly specific polyclonal antibodies is described in copending U.S. Ser. No. 468,393 (filed Jan. 22, 1990 by Reynolds et al, now abandoned). This method generally calls for injecting a mammal with an immunizing amount of an antigen a first time, injecting the mammal a second time between the second and fourteenth days after the first injection with a boosting amount of the antigen, and beginning the fifteenth day after the first injection, injecting the mammal at least three times every seven day period for at least four seven-day periods with a boosting amount of antigen. An immunizing amount and boosting amount can be readily determined by a skilled worker in the art. After the last booster injection, antisera is removed from the mammal.

After extraction of antigen and provision of antibodies specific to that antigen, the method of this invention is carried out by forming a detectable immunological complex of the antigen and antibody. This complex formation can be accomplished in a number of procedures and the present invention is not limited to a specific procedure even though the "sandwich" assays described in detail below are most preferred.

In one embodiment, the extracted antigen can be insolubilized by direct adsorption or covalent attachment to a solid substrate, such as polymeric or glass particles, filtration membranes, cellulosic filter papers, solid polymeric or resin-coated films, glass slides or walls of test tubes, glass or polymeric cuvettes and other substrates readily determinable by one of ordinary skill in the art. Such assays are generally known in the art as "direct binding" assays whereby the antigen directly binds to the substrate, and antibodies are used to complex with the insolubilized antigen. The antibodies can be detectably labeled to make the complex detectable, or the complex can be detected using an anti-antibody which is suitably labeled and specific to the first unlabeled antibody. Detection of the complex can be effected after washing using known techniques. Further details of how direct binding assays are carried out are provided for example in U.S. Pat. No. 4,497,899 (issued Feb. 5, 1985 to Armstrong et al) and copending U.S. Ser. No. 468,045 (filed Jan. 22, 1990 by Snyder et al which was issued as U.S. Pat. No. 5,212,061 on May 18, 1993).

Another embodiment of the method of this invention is an agglutination method whereby antibodies to the extracted antigen are affixed to small particles in some manner and the particles which are detectable by light scattering or by the presence of a tracer such as dye or radioisotope within the particles. The resulting immunoreactive complex is formed through the reaction of antigen with antibodies on the particles, and can be detected using known procedures after washing. Technical details regarding agglutination assays are provided, for example, in U.S. Pat. No. 4,847,199 (issued Jul. 11, 1989 to Snyder et al).

Still other embodiments include competitive immunoassays and enzyme-linked immunoabsorbent assays (known as ELISA) which are generally described in U.S. Pat. No. 4,427,782 (issued to Jan. 24, 1984 to Caldwell et al) and by Schmeer et al, *J. Clin. Microbiol.*, 15(5), pp. 830–834, 1982.

A preferred embodiment of this invention is an immunometric or sandwich assay in which the extracted antigen is reacted at different epitopic sites with two antibodies, one of which is detectably labeled, and the second being immobilized (or capable of being immobilized such as through avidin-biotin or other specific binding reactions). Suitable substrates on which one antibody is immobilized include those noted above for direct binding assays. Preferably, particulate carrier materials formed from organisms, natural or synthetic polymers, glass, ceramics, diatomaceous earth or magnetizable particles are used. These particles are more preferably polymeric, spherical in shape and have an average particle size (in largest dimension) of from about 0.01 to about 10 $\mu$meters, although the size, structural and spatial configurations are not critical. The general procedures for immunometric assays are described, for example, in U.S. Pat. No. 4,376,110 (issued Mar. 8, 1983 to David et al) and U.S. Pat. No. 4,486,530 (issued Dec. 4, 1984 to David et al).

The antibodies can be attached to particulate carrier materials to form water-insoluble immunological reagents by physical or chemical means, including adsorption or covalent reaction with reactive groups on the surface of the materials. Covalent attachment is preferred for optimal assay sensitivity. Many useful reactive groups are known in the art for antibody attachment, which groups can be part of the chemical structure of the carrier material, or added by coating or chemical treatment of an inert material. One skilled in the art would readily understand how to prepare such materials to have any of the following reactive groups: carboxy, 2-substituted ethylsulfonyl, vinylsulfonyl, epoxy, aldehyde, active halo atoms, amino, hydrazide and active esters such as succinimidoxy carbonyl.

Particularly useful particulate carrier materials are polymeric beads described, for example, in EP-A-0,323,692 (published Jul. 12, 1989) which are prepared from one or more ethylenically unsaturated polymerizable monomers having an active halo atom, activated 2-substituted ethylsulfonyl or vinylsulfonyl groups. Other particularly useful particles having reactive carboxy groups are described in copending U.S. Ser. No. 654,112 (filed Feb. 12, 1991 by Ponticello et al).

Homo- and copolymers described in EP-A-0,323, 692 include the following representative materials: poly(m & p-chloromethylstyrene), poly(styrene-co-m & p-chloromethylstyrene-co-2-hydroxyethyl acrylate) (67:30:3 molar ratio), poly[styrene-co-m & p-(2-chloroethylsulfonylmethyl)styrene] (96:4 molar ratio), poly{styrene-co-N-[m & p-(2-chloroethylsulfonylmethyl)-phenyl]acrylamide} (99.3:0.7 molar ratio), poly(m & p-chloromethylstyrene-co-methacrylic acid) (95:5 molar ratio), poly[styrene-co-m & p-(2-chloroethylsulfonylmethyl)styrene-co-methacrylic acid] (93.5:4.5:2 molar ratio) and poly[styrene-co-4-(2-chloroethylsulfonylmethyl)styrene] (95.5:4.5 molar ratio).

Procedures for attaching antibodies to particles having reactive groups are well known, as described for example in U.S. Pat. No. 3,925,157 (issued Dec. 9, 1975 to Hamsher), U.S. Pat. No. 4,181,636 (issued Jan. 1, 1980 to Fischer), U.S. Pat. No. 4,703,018 (issued Oct. 27, 1987 to Craig et al) and EP-A-0,323,692. In general, the antibodies are mixed with the particles under suitable conditions depending upon the attachment form (adsorption, covalent or use of a linking group). A worker skilled in the art would readily know what conditions should be used for each procedure. For example, for attachment to particles having reactive halo atoms, activated 2-substituted ethylsulfonyl or vinylsulfonyl groups, the antibodies are generally mixed with the particles for up to 24 hours at a temperature of from about 20° to about 40° C. in a suspension buffered at a pH of from about 7 to about 10. If carboxy groups are used for attachment, the well known carbodiimide activators can be used, as well as carbomoylonium compounds are described in EP-A-0,308, 235 (published Apr. 22, 1989). Antibodies can be absorbed on particles by incubating particles and antibodies in suspension at suitable temperature for several hours.

More preferably, the immunological reagents described above are coated or deposited on a microporous filtration membrane which is inert to chemical or biological reactions. It is generally composed of one or more natural or synthetic substances which have sufficient integrity for reagents to react or be affixed thereto without loss of form or function. It is porous enough for filtration needed to remove substantially all uncomplexed materials from the complexes formed thereon. Useful membrane materials include, but are not limited to, porous natural or synthetic polymers, sintered glass, membranes of glass or polymeric films or fibers, ceramic materials, cellulosic materials and particulate structures composed of beads bound together with an adhesive or binder material. The membranes are generally flat, but some irregularities in the surfaces are acceptable, as well as some curvature if it is desired. One skilled in the art would be able to identify other useful materials which are commercially available or prepared using known techniques. Particularly useful materials are treated or untreated polyamide microporous membranes such as those commercially available from Pall Corp. under the trademarks LOPRODYNE and BIODYNE.

The membrane generally has an average pore size in the largest dimension of from 0.5 to about 5 μmeters, although smaller or larger pores would be acceptable as long as the complexes formed remain on the membrane and fluid drainage is not adversely affected.

If desired, the membrane can be coated with surfactant or nonimmunoreactive protein (such as casein or succinylated casein), as known in the art to reduce nonspecific interactions or to promote desired filtration.

The wafer-insoluble immunological reagents having appropriate antibodies can be affixed to the membrane over its entire surface or in defined regions thereof. Affixation is accomplished using any mechanical means such as coating, dipping, printing or spraying or fixed by covalent means. Generally, they are coated and dried on the membrane prior to use. They can be used in admixture with hydrophilic binders to provide additional integrity to the coating.

The membrane can be hand held in the assay to provide sites for complexation of extracted antigen and the antibodies thereon. However, preferably, the membrane is disposed or mounted in a disposable test device or article having a suitable frame and structure for holding the membrane and fluid which is drained therethrough. Many such test devices are known in the art, including but not limited to those shown in U.S. Pat. No. 3,825,410 (issued Jul. 23, 1974 to Bagshawe), U.S. Pat. No. 3,888,629 (issued Jun. 10, 1975 to Bagshawe), U.S. Pat. No. 3,970,429 (issued Jul. 20, 1976 to Updike), U.S. Pat. No. 4,446,232 (issued May 1, 1984 to Liotta), U.S. Pat. No. 4,833,087 (issued May 23, 1989 to Hinckley), U.S. Pat. No. 4,847,199 (issued Jul. 11, 1989 to Snyder et al), U.S. Pat. No. 4,921,677 (issued May 1, 1990 to Hinckley et al) and U.S. Pat. No. 4,923,680 (issued May 8, 1990 to Nelson). Particularly useful test devices are those marketed by Eastman Kodak Company under the trademark SURECELL test devices.

Preferred test devices have three test wells designed for providing both negative and positive control results as well as a specimen test result. Each test well contains a membrane as described herein.

Once the water-insoluble complex of antigen and antibodies is formed (preferably on the membrane), the complex is washed with a suitable wash composition (many of which are known in the art and comprise one or more nonionic or anionic surfactants) to remove uncomplexed materials prior to detection of the complex. A preferred wash composition is described below in relation to the examples. A most preferred wash composition is described in copending and commonly-assigned U.S. Ser. No. 774,019 filed on even date herewith by Boyer et al and entitled "Wash Composition, Test Kit and Method for Determination of Microorganisms Associated with Periodontal Diseases" now U.S. Pat. No. 5,248,595, issued Sep. 28, 1993.

If the complex is on a substrate that does not allow fluid drainage, the uncomplexed materials and fluid can be decanted off or otherwise removed. Where a membrane or filter is used, the fluid and uncomplexed materials flow through the membrane or filter and the complex of interest is left thereon.

Depending upon the means of detection, the water-insoluble complex can then be detected using a number of standard reagents and methods. For example, the complex may be detected without tracers or signal producing labels using light scattering techniques known in the art. Agglutinates can be similarly detected.

Preferably, however, whether the assay format is a direct binding assay or immunometric assay, the immunological complex is detected by means of a detectable label on a water-soluble receptor (such as an antibody) for the ligand. Such labels can include, but are not limited to enzymes, avidin, biotin, radioisotopes, fluorogens and chromogens. Enzymes are preferred and can be used to generate colorimetric, fluorometric or chemiluminescent signals which can be evaluated with the unaided eye or using standard spectrophotometric equipment to measure electromagnetic density, spectra or intensity. Useful enzymes include, but are not limited to peroxidase, urease, alkaline phosphatase, acid phosphatase, glucose oxidase, $\beta$-galactosidase and glucosidase. Alkaline phosphatase and peroxidase are preferred with peroxidase being most preferred.

For a given enzyme label, there are various known compositions which provide detectable colorimetric, fluorometric or chemiluminescent signals in the presence of the enzyme. For example, one preferred embodiment utilizes a dye-providing composition which provides a dye in the presence of the enzyme through one or more chemical reactions. A number of leuco dyes are known to be useful for this purpose where peroxidase is the label including those described in U.S. Pat. No. 4,089,747 (issued May 16, 1978 to Bruschi) and U.S. Pat. No. 4,670,386 (issued Jun. 2, 1987 to Babb et al). A preferred dye-providing composition is illustrated in the examples below.

Alternatively, the enzyme label can be used in one or more reactions to produce a chemiluminescent signal, such as described for example in U.S. Pat. No. 4,647,532 (issued Mar. 3, 1987 to Watanabe et al), U.S. Pat. No. 4,835,101 (issued May 30, 1989 to Kao et al), U.S. Pat. No. 4,729,950 (issued Mar. 8, 1988 to Kricka et al) and U.S. Pat. No. 4,598,044 (issued Jul. 1, 1986 to Kricka et al). Other labels besides enzymes can also be used to produce chemiluminescent signals.

In the preferred immunometric assay, at some point the antigen is contacted with a detectably labeled water-soluble antibody. This can occur prior to, simultaneously with or subsequent to the formation of the immunological complex, but generally prior to washing with a wash composition. Thus, the complex of antigen and two antibodies is left on the preferred membrane when uncomplexed materials are washed through. Following formation of this sandwich complex and washing, detection is carried out using reagents and procedures described generally above.

Positive or negative controls can be carried out simultaneously with assay of the specimen. Depending upon the signal being produced for detection, appropriate reagents can be added to stop signal production, for example by adding reagents to stop the formation of a dye, or the production of light by chemiluminescence. These materials are well known in the art.

In a preferred method for the determination of a microorganism associated with periodontal disease, the method comprises the steps of:

A. extracting an antigen from a specimen containing a microorganism associated with periodontal disease with an aqueous extraction composition buffered to a pH of at least about 8 comprising:
  a. at least about 0.05 weight percent of a water-soluble cationic surfactant, and
  b. at least about 0.05 weight percent of an anionic surfactant,
  the contacting being carried out under time and temperature conditions effective to extract an antigen from the microorganism,
B. contacting the extracted antigen with a microporous filtration membrane having thereon, in a discrete zone of a surface of the membrane, a waterinsoluble reagent comprising water insoluble particles having affixed thereto antibodies specific to the antigen, to form, in the zone, a water insoluble complex between the antibody and the antigen,
C. contacting the water-insoluble complex with a detectably labeled second antibody specific to the antigen to form a detectably labeled, water-insoluble sandwich complex in the zone,
D. simultaneously or subsequently to step B, separating uncomplexed materials from the labeled water-insoluble sandwich complex by washing the uncomplexed materials through the membrane, and
E. detecting the labeled, water insoluble sandwich complex as a determination of the microorganism in the specimen.

More preferably, the method just described is useful for the simultaneous determination or differentiation of a plurality of such microorganisms wherein the membrane has a plurality of distinct and independent zones containing distinct water-insoluble reagents for each of the specific microorganisms of interest. Any or all of the microorganisms *Actinobacillus actinomycetemcomitans, Prevotella intermedia* and *Porphyromonas gingivalis* can be determined in this manner.

The method of this invention is generally carried out at room temperature (for example, 18°-25° C.), but higher or lower temperatures may be useful in a given protocol, and certain steps may be carried out at higher temperatures to enhance complexation or other phenomena. In preferred immunometric (sandwich) assays, room temperature is commonly used.

The time of the assay can also vary depending upon the type of assay format and there is no intention to limit the present invention to a particular time or format. However, for the preferred immunometric assays carried out using microporous filtration membranes, the time for the assay (including extraction) may be from about 2 to about 20 minutes.

The following examples are included to illustrate the practice of this invention, and are not meant to be limiting in any way. All percentages are by weight unless otherwise noted.

MATERIALS AND METHODS FOR EXAMPLES

SURECELL TM disposable test devices were used containing LOPRODYNE TM nylon microporous filtration membranes (5 μmeters average pore size) incorporated into the three test wells. The membrane was used after coating with FC𝑣 135 nonionic surfactant (3M Corporation).

The wash solution comprised sodium decyl sulfate (1.8%) in phosphate buffered saline solution (pH 7.2).

A dye-providing composition was prepared to include 4,5-bis(4-methoxyphenyl)-2-(3,5-dimethoxy-4-hydroxyphenyl)imidazole leuco dye (0.008%), poly(vinyl pyrrolidone) (1%), sodium phosphate buffer (10 mmolar, pH 6.8), hydrogen peroxide (10 mmolar), 4'-hydroxyacetanilide (2 mmolar) and diethylenetriaminepentaacetic acid (10 μmolar).

The dye stop solution comprised sodium azide (0.1%) in phosphate buffered saline solution.

Various extraction compositions were tried, as described below.

Polyclonal antibodies directed against each of the three microorganisms *Actinobacillus actinomycetemcomitans* (*A.a.*), *Prevotella intermedia* (*P.i.*) and *Porphyromonas gingivalis* (*P.g.*) were prepared by intravenous injection of rabbits according to the protocol described in U.S. Ser. No. 468,393 (noted above). IgG fractions were prepared by ammonium sulfate precipitation, and stored at 4° C. in phosphate buffered saline solution (0.3–0.4% solution). The bacterial strains used to produce the antisera were supplied as viable cultures by H.S. Reynolds (SUNY, Buffalo School of Dentistry). Isolates were subcultured on anaerobic plates. The microorganisms were those identified by the deposit numbers of ATCC 43717, ATCC 43718 and ATCC 43719 for *A.a.* (serotypes A, B and C, respectively), ATCC 25611, NCTC 9336 and ATCC 49046 for *P.i.* (serotypes A, B and C, respectively) and ATCC 33277, ATCC 53978 and ATCC 53977 for *P.g.* (serotypes A, B and C, respectively). ATCC is the American Type Culture Collection (Rockville, Md.) and NCTC is the National Collection of Type Cultures (London, U.K.).

Water insoluble reagents were prepared by covalently binding antibodies specific to each microorganism (all of serotypes A, B and C) to polymeric particles (1 μmeter average diameter) of poly[styrene-co-4-(2-chloroethylsulfonylmethyl)styrene] (95.5:4.5 molar ratio) which had been prepared using the procedures of EP-A-0,323,692 (noted above). Covalent attachment was achieved by adding the antibodies specific to a given microorganism (0.75 mg/ml final solution with 0.25 mg/ml of each serotype A, B and C) to a solution of borate buffer (0.05 molar, pH 8.5) in a test tube and mixing well. The polymeric particles (3% solids) were added to the buffered mixture, and the resulting suspension was rotated endover-end for 4–24 hours at room temperature to allow covalent attachment of the antibodies to the particles. The suspension was then centrifuged at 2800 rpm for 10 minutes. The supernatant was discarded and the pellet was suspended in glycine buffer (0.1%, pH 8.5) containing merthiolate (0.01%).

A coating suspension of the reagent described above (0.95% solids) was prepared to have polyacrylamide binder (5%), in glycine buffer (0.1 molar, pH 8.5). Each reagent directed to a distinct antigen was coated in defined regions of the membrane in the test devices described above.

Enzyme-antibody conjugates were prepared using antibodies directed to each microorganism conjugated to horseradish peroxidase using the procedure of Yoshitake et al, *Eur. J. Biochem.*, 101, 395, 1979. Each conjugate composition comprised the conjugates (7.5–15 μg of each antibody per ml) added to a solution of casein [0.5%, from a 1% solution in 0.1 molar 3-(N-morpholino)propanesulfonic acid buffer, pH 7.5], TWEEN TM 20 nonionic surfactant (0.3%), merthiolate (0.01%), 4'-hydroxyacetanilide (10 mmolar) in buffer (0.1 molar, pH 7.5). The amount of antibody specific for A.a. (all serotypes) and P.g. (all serotypes) was 10 µg/ml. For P.i. (serotypes A and C), the amount was 7 5 µg/ml and for serotype B it was 15 µg/ml.

All other reagents were obtained from Eastman Kodak Company or other well known suppliers of chemicals and reagents.

EXAMPLE 1

PREFERRED EXTRACTION COMPOSITION AND COMPARISONS OF ASSAYS USING VARIOUS EXTRACTION COMPOSITIONS

A preferred extraction composition used in this invention was prepared by mixing sodium dodecyl sulfate anionic surfactant (5%) and EMCOL TM CC-9 cationic surfactant (5%) in glycine buffer (0.1 molar, pH 8.5). A comparison was made using various conventional extraction compositions.

In the comparisons, the control assays were carried out using the following compositions for antigen extraction:
Control A: Distilled water.
Control B: Phosphate buffered saline solution (0.05 molar, pH 7.3).
Control C: Sodium dodecyl sulfate (0.1%) in water.
Control D: Sodium dodecyl sulfate (1%) in water.
Control E: Sodium dodecyl sulfate (10%) in water.
Control F: Sodium dodecyl sulfate (0.1%) in glycine buffer (0.1 molar, pH 8.5).
Control G: Sodium dodecyl sulfate (10%) in glycine buffer (0.1 molar, pH 8.5).
Control H: Sodium dodecyl sulfate (10%) in succinate buffer (0.1 molar, pH 4.5).
Control I: EMCOL TM CC-9 cationic surfactant (7.5%) in glycine buffer (0.1 molar, pH 8.5).

Extraction Procedure

Each extraction composition was used in the following manner. An appropriate volume of a stock solution of microorganisms ($1 \times 10^9$ cells/ml) was mixed with the extraction composition for about 1 minute at room temperature to yield the desired cell concentration. The amount of cells in the final solution was as follows:

For the data provided in Table I below, for *Actinobacillus actinomycetemcomitans* (*A.a.*), serotypes A and B, antigen dilution "12" contained $9.8 \times 10^5$ cells/ml, antigen dilution "14" contained $2.4 \times 10^5$ cells/ml, and antigen dilution "18" contained $1.5 \times 10^4$ cells/ml. For serotype C, antigen dilution "10" contained $3.9 \times 10^6$ cells/ml, antigen dilution "14" contained $2.4 \times 10^5$ cells/ml and antigen "16" contained $6.0 \times 10^4$ cells/mi.

For the data provided in Table II below, for *A.a.*, all serotypes, antigen dilution "10" contained $3.9 \times 10^6$ cells/ml, antigen dilution "14" contained $2.4 \times 10^5$ cells/ml, and antigen dilution "18" contained $1.5 \times 10^4$ cells/mi. For *Prevotella intermedia* (*P.i.*) and *Porphyromonas gingivalis* (*P.g.*), antigen dilution "5" contained $1.3 \times 10^8$ cells/ml, antigen dilution "8" contained $1.6 \times 10^7$ cells/ml, and antigen dilution "11" contained $2.0 \times 10^6$ cells/mi.

Assay Procedure

A sample (50 µl) of each extractant provided above from the extraction procedure was added to each test well of a disposable test device as described above and fluid was allowed to drain through the membranes in the test wells as the extracted antigen complexed with the immunological reagent (containing antibodies) on the membranes.

Immediately, the conjugate of peroxidase and antibody (40 µl) was added to the well and sandwich complex formation was allowed for 5 minutes incubation at room temperature.

Each test well was half filled with the wash solution (about 400 µl) which then drained through the membrane. This was repeated once.

After the last wash, the dye-providing composition (40 µl) was added to each test well followed by a 2 minute incubation at room temperature.

The resulting dye signal was then visually evaluated and compared to a calibrated color chart containing reflectance density values. The reflection densities were then converted to transmission density ($D_T$) values using the conventional Williams-Clapper transformation (see *J. Optical Soc. Am.*, 43, 595, 1953). The results were then tabulated as shown below. $D_T$ values of 0.003 or less correspond to a visual evaluation or "no dye signal".

The results, as seen in the tables below are explained as follows. Table I shows data from assays of extracted antigens from serotypes A, B and C of *A.a.* using Controls A–E. As the amount of sodium dodecyl sulfate used in the composition was increased, the background signals were decreased, but the sensitivity to extracted antigen from serotypes B and C steadily decreased. This is highly undesirable, of course, because it is clinically important to detect all three serotypes of this microorganism to have a commercially viable assay.

TABLE I

| A.a. Serotype | Antigen Dilution # | Dye Signals ($D_T$) | | | | |
|---|---|---|---|---|---|---|
| | | Control A | Control B | Control C | Control D | Control E |
| A | 12 | 0.057 | 0.114 | 0.114 | 0.145 | 0.195 |
| | 14 | 0.022 | 0.057 | 0.057 | 0.089 | 0.145 |
| | 18 | neg* | neg* | 0.019 | 0.022 | 0.019 |
| B | 12 | 0.042 | 0.101 | 0.114 | 0.114 | 0.073 |
| | 14 | 0 019 | 0.027 | 0.057 | 0.042 | 0.026 |
| | 18 | neg* | neg* | 0.015 | 0.019 | neg* |
| C | 10 | 0.114 | 0.114 | 0.185 | 0.145 | 0.114 |
| | 14 | neg* | neg* | 0.027 | 0.019 | neg* |
| | 16 | neg* | neg* | 0.015 | neg* | neg* |

*neg = negligible signal

Further results are illustrated in Table II below where several other control extraction compositions were compared to that used in Example 1. Putting sodium dodecyl sulfate in glycine buffer (pH 8.5, Controls F and G) somewhat improved the sensitivity of the assays, especially for serotypes B and C of *A.a.* Sodium dodecyl sulfate in an acidic medium (Control H) was no better than Control G using the same amount of surfactant at high pH. Using the cationic surfactant alone (Control I) improved the sensitivity for antigens of serotypes B and C, but the sensitivity for the serotype A antigen was unacceptable.

Only Example 1, using a composition containing both cationic and anionic surfactants at high pH, provided desired extraction and sensitivity of all serotypes of *A.a.* without losing any sensitivity to the antigens extracted from all serotypes of *P.i.* and *P.g.*, and at the same time keeping the background signals acceptably low.

TABLE II

| Micro-organism Serotype | Antigen Dilution # | Dye Signals ($D_T$) | | | | |
|---|---|---|---|---|---|---|
| | | Control F | Control G | Control H | Control I | Example 1 |
| A.a. A | 10 | 0.114 | 0.175 | 0.145 | 0.145 | 0.175 |
| | 14 | 0.073 | 0.101 | 0.073 | 0.042 | 0.073 |
| | 18 | 0.022 | 0.024 | neg* | 0.004 | 0.024 |
| A.a. B | 10 | 0.101 | 0.145 | 0.114 | 0.101 | 0.114 |
| | 14 | 0.022 | 0.025 | 0.005 | 0.024 | 0.025 |
| | 18 | neg* | 0.005 | neg* | 0.015 | 0.015 |
| A.a C | 10 | 0.101 | 0.101 | 0.101 | 0.114 | 0.114 |
| | 14 | 0.022 | 0.022 | neg* | 0.027 | 0.025 |
| | 18 | neg* | neg* | neg* | 0.004 | 0.018 |
| P.g. A | 5 | 0.215 | 0.215 | 0.215 | 0.215 | 0.215 |
| | 8 | 0.185 | 0.195 | 0.185 | 0.185 | 0.195 |
| | 11 | 0.114 | 0.145 | 0.101 | 0.101 | 0.175 |
| p.g. B | 5 | 0.215 | 0.215 | 0.205 | 0.185 | 0.215 |
| | 8 | 0.175 | 0.185 | 0.175 | 0.175 | 0.185 |
| | 11 | 0.089 | 0.101 | 0.101 | 0.101 | 0.114 |
| P.g. C | 5 | 0.215 | 0.215 | 0.215 | 0.185 | 0.205 |
| | 8 | 0.175 | 0.175 | 0.175 | 0.175 | 0.185 |
| | 11 | 0.073 | 0.073 | 0.073 | 0.101 | 0.101 |
| P.i. A | 5 | 0.215 | 0.215 | 0.215 | 0.195 | 0.215 |
| | 8 | 0.185 | 0.195 | 0.175 | 0.145 | 0.195 |
| | 11 | 0.114 | 0.101 | 0.101 | 0.114 | 0.114 |
| P.i. B | 5 | 0.175 | 0.185 | 0.175 | 0.114 | 0.195 |
| | 8 | 0.145 | 0.101 | 0.101 | 0.073 | 0.114 |
| | 11 | 0.042 | 0.025 | 0.022 | 0.024 | 0.022 |
| P.i. C | 5 | 0.175 | 0.195 | 0.175 | 0.114 | 0.215 |
| | 8 | 0.114 | 0.145 | 0.114 | 0.089 | 0.175 |
| | 11 | 0.024 | 0.042 | 0.042 | 0.024 | 0.057 |

*neg = negligible dye signal

EXAMPLE 2

SANDWICH ASSAY USING PREFERRED EXTRACTION AND WASH COMPOSITIONS

This example demonstrates the use of a preferred extraction composition (Example 1) with a preferred wash composition described in copending U.S. Ser. No. 774,019 (filed on even date herewith by Boyer, Contestable and Snyder, entitled "Wash Composition, Test Kit and Method for Determination of Microorganisms Associated with Periodontal Diseases"now U.S. Pat. No. 5,248,595 issued Sep. 28, 1993).

Wash Compositions

The wash composition used was composed of TERGITOL ™ 4 anionic surfactant (2.7%) in phosphate buffer (0.1 molar, pH 10).

Assay Procedure

Antigen from ATCC 53978 [serotype B, P.g.] was extracted by subjecting the cells to the extraction composition used in Example 1 for a few seconds at room temperature to achieve a final concentration of 1.25 × $10^8$ total cells/ml.

The extract (450 μl)was filtered through a 1.2 μmeter membrane and added to one test well of the test device described above. The membrane of the test device had defined regions of reagents specific for each of A.a., P.g. and P.i. Fluid was allowed to drain through the membrane in the test well. Antibody conjugate composition (80 μl) was immediately added to each test well followed by incubation for two minutes at room temperature (about 20°-25° C.). The wash solution (500 μl) was then added to each test well and allowed to drain, followed by a second wash (500 μl).

A dye-providing composition (80 μl) like that described above (except comprising 0.5 mmolar of 4'-hydroxyacetanilide) was added to each test well followed by a one minute incubation at room temperature.

The dye signal was then visually evaluated and compared to a calibrated color chart containing reflectance density values. The reflection densities were then converted to transmission density ($D_T$) using the Williams-Clapper transformation [see J. Optical Soc. Am., 43, p. 595 (1953)]. $D_T$ values of 0.003 or less correspond to a visual evaluation of "no dye signal".

The results were then tabulated as follows in Table III.

TABLE III

| Assay | $D_T$ Dye Signal | | |
|---|---|---|---|
| | P.g. Reagent | P.i. Reagent | A.a. Reagent |
| Example 2 | 0.101 | 0.003 | 0.003 |

The invention has been described in detail with particular reference to preferred embodiments thereof, but it will be understood that variations and modifications can be effected within the spirit and scope of the invention. All patents, patent applications (published or unpublished, domestic or foreign), scientific literature, books and other prior art cited herein are each incorporated herein by reference for the teaching therein pertinent to this invention.

We claim:

1. A diagnostic test kit comprising, in separate packaging:
   (1) an aqueous extraction composition buffered to a pH of from about 8 to about 11 comprising:
      a. from about 1 to about 10 weight percent of a water-soluble cationic surfactant which is a quaternary ammonium salt or a mixture thereof, and
      b. from about 1 to about 10 weight percent of an anionic surfactant which has a sulfate anion having from 6 to 14 carbon atoms and an alkali metal or ammonium cation, and
   (2) at least one kit component selected from the group consisting of:
      (a) a detectably labeled, water-soluble antibody specific to Actinobacillus actinomycetemcomitans, Porphyromonas gingivalis or Prevotella intermedia, and
      (b) an antibody for Actinobacillus actinomycetemcomitans, Porphyromonas gingivalis or Prevotella intermedia, which antibody is insolubilized, or capable of being insolubilized.

2. The kit of claim 1 wherein said cationic surfactant is a quaternary ammonium salt of polypropoxy-t-amine or a mixture thereof, and said anionic surfactant has either a dodecyl sulfate or decyl sulfate anion and an alkali metal cation.

3. The kit of claim 1 further comprising at least one kit component selected from the group consisting of:
   (1) a disposable test device;
   (2) a wash composition for separating uncomplexed materials from a complex of an antigen extracted from Actinobacillus actinomycetemcomitans, Porphyromonas gingivalis or Prevotella intermedia and an antibody specific thereto, said compositions comprising at least one surfactant; and
   (3) a composition for providing a colorimetric or chemiluminescent signal in the presence of an enzyme label.

4. A method for the extraction of an antigen from Actinobacillus actinomycetemcomitans, Porphyromonas gingivalis or Prevotella intermedia comprising:

contacting a specimen suspected of containing *Actinobacillus actinomycetemcomitans*, *Porphyromonas gingivalis* or *Prevotella intermedia* with an aqueous composition buffered to a pH of from about 8 to about 11 comprising:

a. from about 1 to about 10 weight percent of a water-soluble cationic surfactant which is a quaternary ammonium salt or a mixture thereof, and b. from about 1 to about 10 weight percent of an anionic surfactant which has a sulfate anion having from 6 to 14 carbon atoms and an alkali metal or ammonium cation, said contacting being carried out under time and temperature conditions effective to extract an antigen from *Actinobacillus actinomycetemcomitans*, *Porphyromonas gingivalis* or *Prevotella intermedia*.

5. The method of claim 10 wherein the time of extraction is from about 10 seconds to about 60 minutes, and the temperature of extraction is from about 15 to about 40° C.

6. A method for the determination of *Actinobacillus actinomycetemcomitans*, *Porphyromonas gingivalis* or *Prevotella intermedia* comprising:

A. contacting a specimen suspected of containing *Actinobacillus actinomycetemcomitans*, *Porphyromonas gingivalis* or *Prevotella intermedia* with an aqueous extraction composition buffered to a pH of from about 8 to about 11 comprising:

a. from about 1 to about 10 weight percent of a water-soluble cationic surfactant which is a quaternary ammonium salt or a mixture thereof, and b. from about 1 to about 10 weight percent of an anionic surfactant which has a sulfate anion having from 6 to 14 carbon atoms and an alkali metal or ammonium cation, said contacting being carried out under time and temperature conditions effective to extract an antigen from said *Actinobacillus actinomycetemcomitans*, *Porphyromonas gingivalis* or *Prevotella intermedia*.

B. after extraction forming a detectable immunological complex of the extracted antigen and an antibody specific to the antigen, and C. detecting said complex as a determination of the presence of *Actinobacillus actinomycetemcomitans*, *Porphyromonas gingivalis* or *Prevotella intermedia* in said specimen.

7. The method of claim 6 wherein the time of extraction is from about 10 seconds to about 60 minutes, and the temperature of extraction is from about 15 to about 40° C.

8. The method of claim 6 wherein said antibody is detectably labeled, and said extracted antigen is also contacted with an unlabeled antibody specific thereto which is insolubilized or capable of being insolubilized during the method.

9. The method of claim 8 wherein the detectably labeled antibody is enzyme labeled, and detection of said complex is accomplished by contacting said complex with a composition which provides a colorimetric or chemiluminescent signal in the presence of said enzyme.

10. The method of claim 6 wherein said complex is separated from uncomplexed materials by washing prior to detection step C.

11. The method of claim 6 wherein *Actinobacillus actinomycetemcomitans*, *Porphyromonas gingivalis* or *Prevotella intermedia* are detected simultaneously in said specimen.

12. The method of claim 6 wherein said detectable immunological complex is formed on a microporous membrane through which uncomplexed materials are drained.

* * * * *